United States Patent
Stevens et al.

(10) Patent No.: US 9,078,451 B2
(45) Date of Patent: Jul. 14, 2015

(54) METHOD FOR EUTHANIZING ANIMALS

(71) Applicants: Brian Stevens, Wolverton, MN (US); David Newman, Wolverton, MN (US)

(72) Inventors: Brian Stevens, Wolverton, MN (US); David Newman, Wolverton, MN (US)

( * ) Notice: Subject to any disclaimer, the term of this patent is extended or adjusted under 35 U.S.C. 154(b) by 10 days.

(21) Appl. No.: 13/782,356

(22) Filed: Mar. 1, 2013

(65) Prior Publication Data
US 2014/0245964 A1 Sep. 4, 2014

(51) Int. Cl.
*A01M 13/00* (2006.01)
*A01K 1/03* (2006.01)
*A22B 3/00* (2006.01)

(52) U.S. Cl.
CPC .. *A22B 3/005* (2013.01); *A01K 1/03* (2013.01)

(58) Field of Classification Search
CPC ............. A01K 1/03; A01K 1/031; A22B 3/00
USPC ........................ 119/418, 420; 452/66; 43/125; 128/203.12
See application file for complete search history.

(56) References Cited

U.S. PATENT DOCUMENTS

| | | | | |
|---|---|---|---|---|
| 3,356,087 | A * | 12/1967 | Guttman | 128/203.12 |
| 4,107,818 | A * | 8/1978 | Scott et al. | 606/1 |
| 4,941,431 | A * | 7/1990 | Anderson et al. | 119/420 |
| 5,584,124 | A * | 12/1996 | Wentworth | 43/124 |
| 5,842,504 | A * | 12/1998 | Schennum et al. | 137/540 |
| 6,352,076 | B1 * | 3/2002 | French | 128/203.12 |
| 6,776,158 | B1 * | 8/2004 | Anderson et al. | 128/203.12 |
| 6,904,912 | B2 * | 6/2005 | Roy et al. | 128/203.18 |
| 7,252,050 | B2 * | 8/2007 | Cole | 119/416 |
| 7,331,341 | B2 * | 2/2008 | Nelson | 128/203.12 |
| 7,341,023 | B2 * | 3/2008 | Caplette | 119/420 |
| 7,549,397 | B2 * | 6/2009 | Caplette | 119/420 |
| 8,029,342 | B2 * | 10/2011 | Anderson et al. | 452/66 |
| 8,196,574 | B2 * | 6/2012 | Ichikawa | 128/203.12 |
| 2005/0178340 | A1 * | 8/2005 | Caplette | 119/420 |
| 2011/0139086 | A1 | 6/2011 | Burgener | |
| 2011/0306676 | A1 | 12/2011 | Dunlop | |
| 2012/0272919 | A1 * | 11/2012 | McClelland | 119/420 |

FOREIGN PATENT DOCUMENTS

| | | | |
|---|---|---|---|
| EP | 1616482 A2 * | 1/2006 | |
| EP | 1 921 921 | 12/2009 | |
| JP | 2007060925 A * | 3/2007 | |
| WO | 2007120973 | 10/2007 | |
| WO | 2007129100 | 11/2007 | |
| WO | 2009058557 | 5/2009 | |

* cited by examiner

*Primary Examiner* — Monica Williams
*Assistant Examiner* — Michael Wang

(57) ABSTRACT

An animal euthanization assembly provides a method for humanely anesthetizing and euthanizing animals using small but effective single doses of agents dispersed from a single one use container. The assembly includes a box having a bottom wall and a perimeter wall coupled to and extending upwardly from the bottom wall defining an interior space of the box. A lid selectively couples to the box wherein the interior space is enclosed. A valve is coupled to the box. A canister has a dispensing nozzle selectively engageable to the valve wherein contents of the canister are dispensed into the interior space of the box when the dispensing nozzle is engaged to the valve. An anesthetizing agent and a euthanizing agent are dispensed from the canister when the dispensing nozzle is engaged to the valve.

13 Claims, 4 Drawing Sheets

METHOD FOR EUTHANIZING ANIMALS

BACKGROUND OF THE DISCLOSURE

Field of the Disclosure

The disclosure relates to animal euthanization devices and more particularly pertains to a new animal euthanization device for humanely anesthetizing and euthanizing animals using small but effective dose of agents dispersed from a single one use canister.

SUMMARY OF THE DISCLOSURE

An embodiment of the disclosure meets the needs presented above by generally comprising a box having a bottom wall and a perimeter wall coupled to and extending upwardly from the bottom wall defining an interior space of the box. A lid selectively couples to the box wherein the interior space is enclosed. A valve is coupled to the box. A canister has a dispensing nozzle selectively engageable to the valve wherein contents of the canister are dispensed into the interior space of the box when the dispensing nozzle is engaged to the valve. An anesthetizing agent is positioned in the canister. A euthanizing agent is also positioned in the canister. The euthanizing agent is dispensed from the canister subsequent to the anesthetizing agent when the dispensing nozzle is engaged to the valve.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
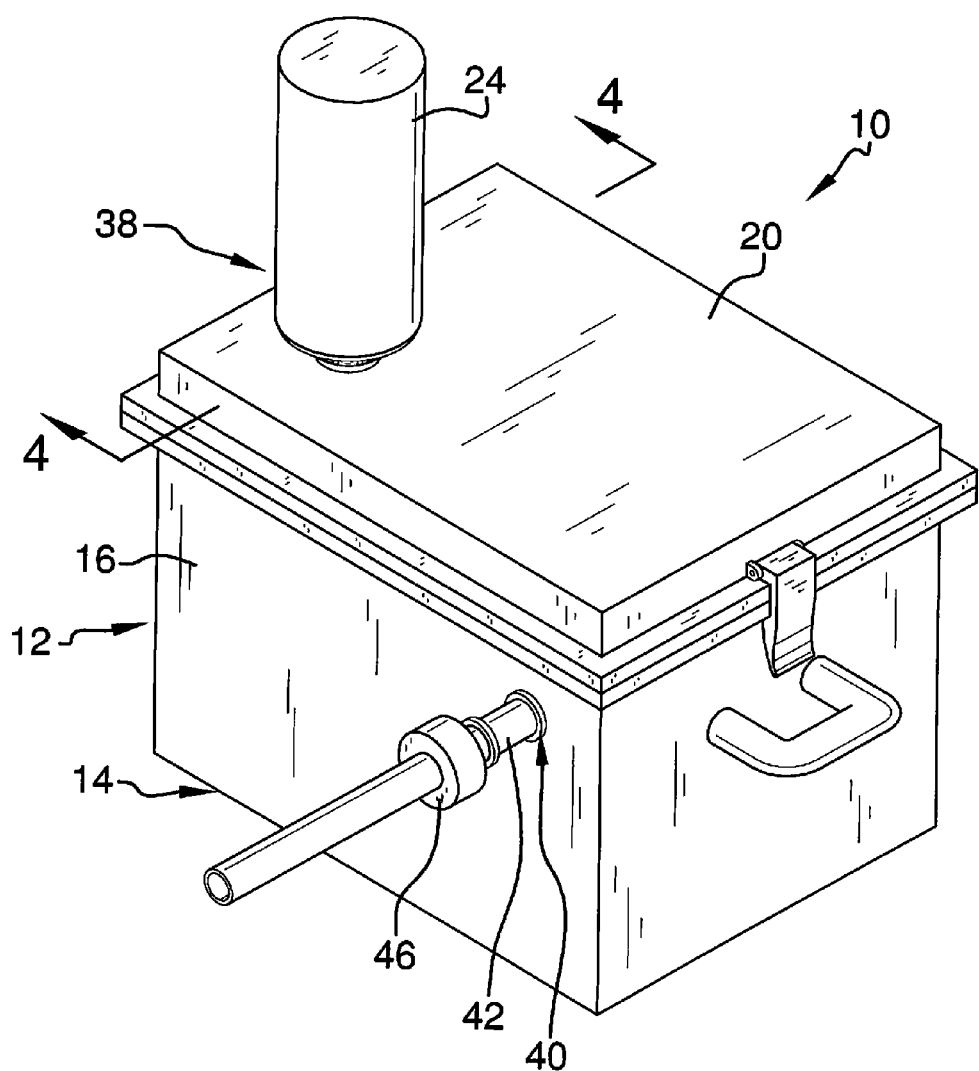
FIG. 1 is a top front side perspective view of an animal euthanization assembly according to an embodiment of the disclosure.
Figure 2:
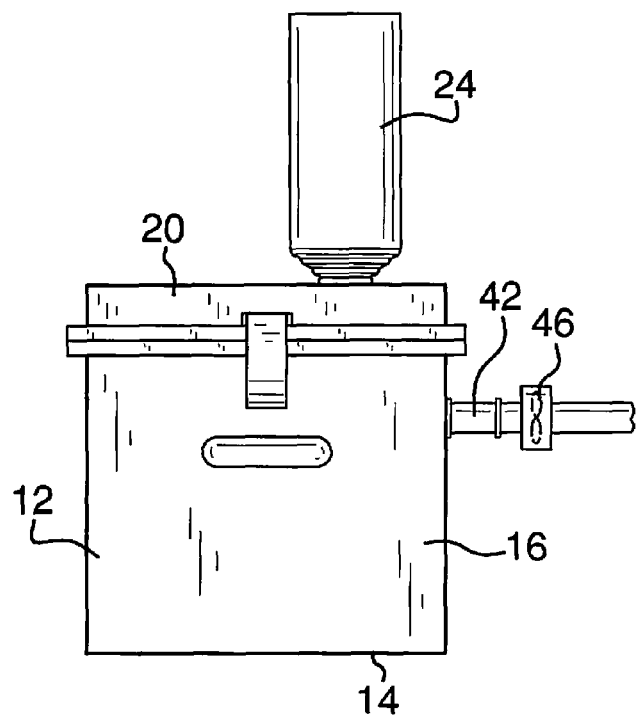
FIG. 2 is a side view of an embodiment of the disclosure.
Figure 3:
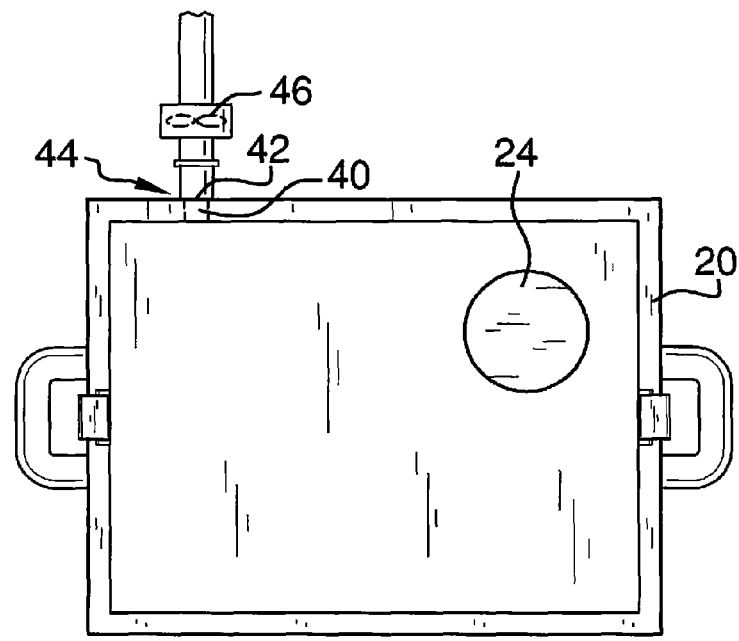
FIG. 3 is a top view of an embodiment of the disclosure.
Figure 4:
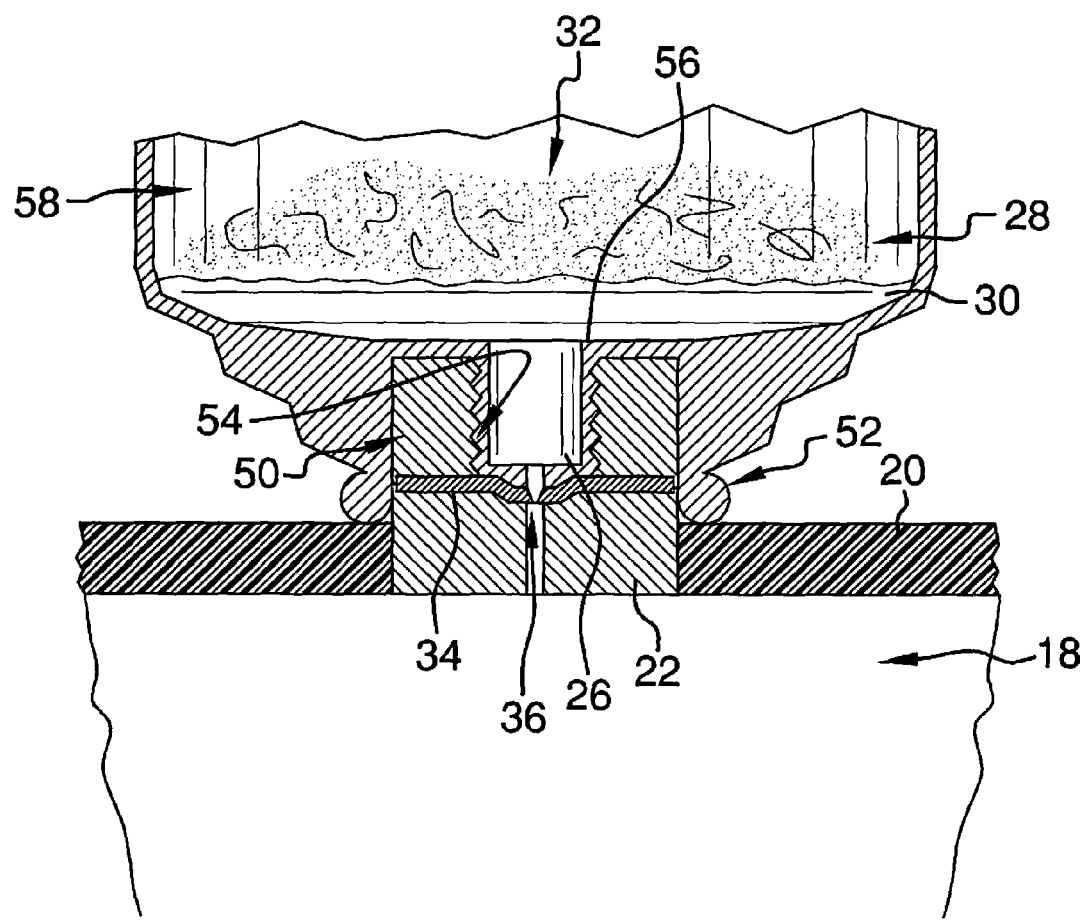
FIG. 4 is a cross-sectional view of an embodiment of the disclosure taken along line 4-4 of FIG. 3.
Figure 5:
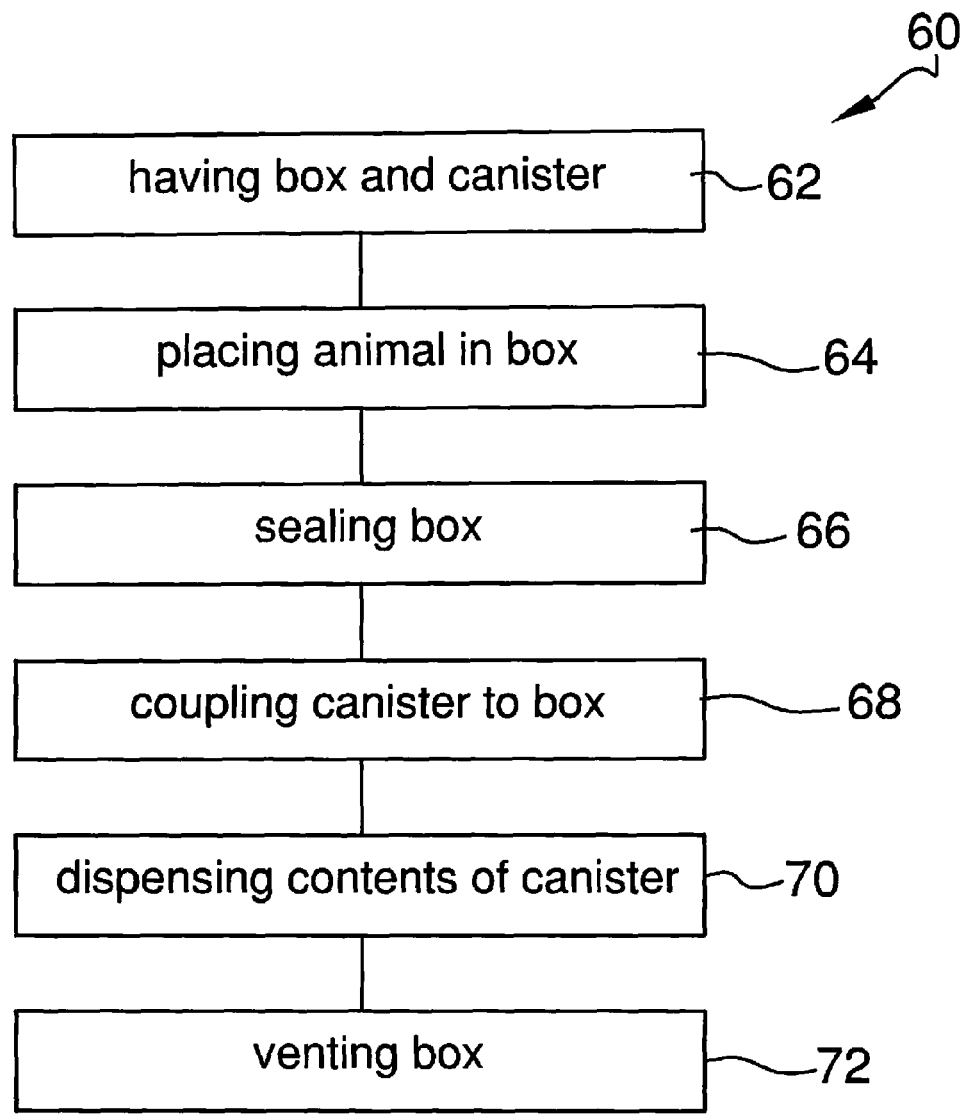
FIG. 5 is a schematic view of a method according to an embodiment of the disclosure.

With reference now to the drawings, and in particular to FIGS. 1 through 5 thereof, a new animal euthanization device embodying the principles and concepts of an embodiment of the disclosure and generally designated by the reference numeral 10 will be described.

As best illustrated in FIGS. 1 through 5, the animal euthanization assembly 10 generally comprises a box 12 having a bottom wall 14 and a perimeter wall 16 coupled to and extending upwardly from the bottom wall 14 defining an interior space 18. A lid 20 is selectively coupled to the box 12 wherein the interior space 18 is enclosed when desired. When the lid 20 is removed from the box 12, an animal to be euthanized may be placed into the interior space 18. A valve 22 is coupled to the box 12. A canister 24 is provided having a dispensing nozzle 26. The dispensing nozzle 26 is selectively engageable to the valve 22 wherein contents 28 of the canister 24 are dispensed into the interior space 18 of the box 12 when the dispensing nozzle 26 is engaged to the valve 22. An anesthetizing agent 30 is positioned in the canister 24 as well as a euthanizing agent 32. The euthanizing agent 32 may be dispensed from the canister 24 simultaneously to or subsequent to the anesthetizing agent 30 when the dispensing nozzle 26 is engaged to the valve 22. When dispensed simultaneously as a mixture into the interior space 18 of the box 12, a concentration of the anesthetizing agent 30 within the interior space 18 of the box 12 relative to a concentration of the euthanizing agent 32 in the interior space 18 of the box 12 is such that the anesthetizing agent 30 anesthetizes the animal prior to the euthanizing agent 32 euthanizing the animal. Thus, through either simultaneous or sequential dispensing, the animal in the box 12 is anesthetized sufficiently to prevent exaggerated movements and discomfort prior to be euthanized.

The lid 20 may fully cover the box 12. The valve 22 extends through the lid 20 wherein the canister 24 is in an inverted position 38 when the dispensing nozzle 26 is engaged to the valve 22. The dispensing nozzle 26 is positioned at a bottom 56 of an interior space 58 of the canister 24 when the canister 24 is in the inverted position 38. To achieve the substantially two stage dispensation for the desired result, the anesthetizing agent 30 is a liquid in the canister 24 such that the anesthetizing agent 30 moves to the bottom 56 of the interior space 58 of the canister 24 in the inverted position 38. When the dispensing nozzle 26 is coupled to the valve 22, the anesthetizing agent 30 is released into the interior space 18 of the box 12 as a mist or gas. The euthanizing agent 32 may be a gas or a liquid having lesser density than the anesthetizing agent 30 while in the canister 24. Thus, although some mixing may occur, the anesthetizing agent 30 is dispensed through the dispensing nozzle 26 in an effective amount prior to the euthanizing agent 32 being dispensed into the interior space 18 of the box 12 as a mist or gas. A propellant 48 is positioned in the canister 24. The propellant 48 facilitates dispensation of the anesthetizing agent 30 and the anesthetic agent 32 from the canister 24 when the dispensing nozzle 26 is coupled to the valve 22.

A restrictor 34 is coupled to the valve 22 or directly to the dispensing nozzle 26 of the canister 24. The restrictor 34 has an opening 36 therethrough sized such that the anesthetizing agent 30 is dispensed through the opening 36 in the restrictor 34 at a pre-selected desired rate to give the anesthetizing agent 30 time to produce the desired effect prior to the effective introduction of the euthanizing agent 32 into the box 12. Thus, the anesthetizing agent 30 anesthetizes the animal in the interior space 18 of the box 12 prior to the euthanizing agent 32 being effectively dispersed into the interior space 18 of the box 12. The anesthetizing agent 30 and the euthanizing agent 32 may each be dispensed into the interior space 18 of the box 12 substantially in sequence by a single connection of the dispensing nozzle 26 to the valve 22.

The anesthetizing agent 30 may be nitrous oxide producing a concentration of between 10% and 50% nitrous oxide within the interior space 18 of the box 12 when the anesthetizing agent 30 is dispersed into the interior space 18 of the box 12. Alternatively, the anesthetizing agent 30 may be isoflurane producing a concentration of between 1% and 8% within the interior space 18 of the box 12 when the anesthetizing agent 30 is dispensed into the interior space 18 of the box 12. The euthanizing agent 32 is a hemoglobin binding agent such as carbon monoxide producing a concentration between 1,000 parts per million and 100,000 parts per million within the interior space 18 of the box 12 when the euthanizing agent 32 is dispersed into the interior space 18 of the box 12. The box 12 is sized such that effective amounts of the anesthetizing agent 30 and the euthanizing agent 32 in the box 12 are not sufficiently large to be a health concern even if fully released from the canister 24 into ambient air outside of the box 12. Thus, individual canisters 24 may be bought, stored, and shipped more easily than large containers requiring hazardous material permits or the like.

A cavity 50 is positioned on a dispensing end 52 of the canister 24. The dispensing nozzle 26 is positioned in the cavity 50. An exterior wall 54 of the dispensing nozzle 26 is threaded. The valve 22 has complimentary threading wherein the canister 24 is threadedly coupled to the box 12 for dispensing the contents of the canister 24 into the interior space 18 of the box 12.

A vent aperture 40 extends through the box 12. A vent closure 42 such as a conventional one-way valve is coupled to the box 12. The vent closure 42 selectively seals the vent aperture 40 wherein the interior space 18 of the box 12 is sealed when the lid 20 is in a closed position 44 and the vent closure 42 is in a closed position. As stated above, the interior space 18 of the box 12 may be vented safely through the vent aperture 40 directly to ambient air. Alternatively, an exhaust mechanism 46 may be coupled to the box 12. The exhaust mechanism 46 is environmentally coupled to the vent closure 42 wherein gaseous contents of the interior space 18 of the box 12 are vented through the vent aperture 40 when the exhaust mechanism 46 is actuated.

In use, the assembly 10 provides for a method 60 of euthanizing an animal. The first step 62 is having the box 12, the valve 22 in environmental communication with the box 12, and the canister 24 as generally described above. Minimally, the box 12 may be as described above but needs only to provide the sealable interior space 18. Another step 64 is placing an animal to be euthanized in the interior space 18 of the box 12. A subsequent step 66 is sealing the animal within the interior space 18 of the box 12. Still another step 68 is coupling the canister 24 to the valve 22 wherein the anesthetizing agent 30 and the euthanizing agent 32 are dispensed into the sealed interior space of the box 12 wherein the animal is anesthetized and subsequently euthanized. A step 70 may be provided of completely dispensing contents of the canister 24 into the interior space 18 of the box 12 upon coupling of the dispensing nozzle 26 to the valve 22 wherein the contents of the canister 24 provide effective concentrations of the anesthetizing agent 30 and the euthanizing agent 32 relative to a volume of the interior space 18 within the box 12. Still another step 72 is venting the interior space 18 of the box 12 after euthanizing the animal and prior to removing the lid 20 from the box 12.

An effective concentration of the anesthetizing agent 30 may be dispensed from the canister 24 prior to an effective amount of the euthanizing agent 32 being dispensed from the canister 24. A single dose or an effective amount, for purposes of the disclosed invention, is an amount of the anesthetizing agent 30 or anesthetic agent 32 sufficient to create the desired effect of anesthetization or euthanasia to one or more animals in the interior space 18. Consistent with the method 60, the anesthetizing agent 30 and the euthanizing agent 32 may be dispensed simultaneously as a mixture into the interior space 18 of the box 12. When dispensed simultaneously, a concentration of the anesthetizing agent 30 within the interior space 18 of the box 12 relative to a concentration of the euthanizing agent 32 in the interior space 18 of the box 12 is such that the anesthetizing agent 30 anesthetizes the animal prior to the euthanizing agent 32 euthanizing the animal. Alternatively, the anesthetizing agent 30 and the euthanizing agent 32 may be dispensed sequentially from the canister 24 into the interior space 18 of the box 12 as described above.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An animal euthanization assembly comprising:
  a box having a bottom wall and a perimeter wall coupled to and extending upwardly from said bottom wall defining an interior space;
  a lid selectively coupled to said box wherein said interior space is enclosed;
  a valve coupled to said box;
  a canister having a dispensing nozzle, said dispensing nozzle being selectively engageable to said valve wherein contents of said canister are dispensed into said interior space of said box when said dispensing nozzle is engaged to said valve, said valve extending through said lid wherein said canister is in an inverted position when said dispensing nozzle is engaged to said valve, said dispensing nozzle being positioned at a bottom of an interior space of said canister when said canister is in said inverted position;
  an anesthetizing agent positioned in said canister, said anesthetizing agent being a liquid in said canister; and
  a euthanizing agent positioned in said canister, said euthanizing agent being a gas in said canister, said euthanizing agent being a different substance than said anesthetizing agent, said euthanizing agent being dispensed from said canister subsequent to said anesthetizing agent when said dispensing nozzle is engaged to said valve.

2. The assembly of claim 1, further comprising a restrictor coupled to said valve, said restrictor having an opening therethrough sized such that said anesthetizing agent is dispensed through said restrictor as a pre-selected rate wherein said anesthetizing agent anesthetizes an animal in said interior space of said box prior to said euthanizing agent being dispersed into said interior space of said box.

3. The assembly of claim 1, further comprising said euthanizing agent being carbon monoxide producing a concentration between 1,000 parts per million and 100,000 parts per million within said interior space of said box when said euthanizing agent is dispersed into said interior space of said box.

4. The assembly of claim 1, further comprising said anesthetizing agent being nitrous oxide producing a concentration of between 10% and 50% nitrous oxide within said interior space of said box when said anesthetizing agent is dispersed into said interior space of said box.

5. The assembly of claim 1, further comprising said anesthetizing agent being isoflurane producing a concentration of between 1% and 8% within said interior space of said box when said anesthetizing agent is dispensed into said interior space of said box.

6. The assembly of claim 1, further comprising said anesthetizing agent and said euthanizing agent each being dispensed into said interior space of said box in sequence by a single connection of said dispensing nozzle to said valve.

7. The assembly of claim 1, further comprising said euthanizing agent being a hemoglobin binding agent.

8. The assembly of claim 1, further comprising:
a vent aperture extending through said box;
a vent closure coupled to said box, said vent closure selectively sealing said vent aperture wherein said interior space of said box is sealed when said lid is in a closed position and said vent closure is in a closed position; and
an exhaust mechanism coupled to said box, said exhaust mechanism being environmentally coupled to said vent closure wherein gaseous contents of said interior space of said box is vented through said vent aperture when said exhaust mechanism is actuated.

9. The assembly of claim 1, further comprising a propellant being positioned in said canister, said propellant facilitating dispensation of said anesthetizing agent and said anesthetic agent from said canister when said dispensing nozzle is coupled to said valve.

10. The assembly of claim 1, further comprising a cavity positioned on a dispensing end of said canister, said dispensing nozzle being positioned in said cavity.

11. The assembly of claim 10, further comprising:
an exterior wall of said dispensing nozzle being threaded; and
said valve having complimentary threading wherein said canister is threadedly coupled to said box for dispensing said contents of said canister into said interior space of said box.

12. An animal euthanization assembly comprising:
a box having a bottom wall and a perimeter wall coupled to and extending upwardly from said bottom wall defining an interior space;
a lid selectively coupled to said box wherein said interior space is enclosed;
a valve coupled to said box; and
a canister having a dispensing nozzle, said dispensing nozzle being selectively engageable to said valve wherein contents of said canister are dispensed into said interior space of said box when said dispensing nozzle is engaged to said valve, said valve extending through said lid wherein said canister is in an inverted position when said dispensing nozzle is engaged to said valve, said dispensing nozzle being positioned at a bottom of an interior space of said canister when said canister is in said inverted position;
an anesthetizing agent positioned in said canister, said anesthetizing agent being a liquid in said canister; and
a euthanizing agent positioned in said canister, said euthanizing agent being a gas in said canister wherein said anesthetizing agent being dispensed through said dispensing nozzle prior to said euthanizing agent being dispensed into said interior space of said box, a concentration of said anesthetizing agent within said interior space of said box relative to a concentration of said euthanizing agent in said interior space of said box being such that said anesthetizing agent anesthetizes the animal prior to said euthanizing agent euthanizing the animal.

13. An animal euthanization assembly comprising:
a box having a bottom wall and a perimeter wall coupled to and extending upwardly from said bottom wall defining an interior space;
a lid selectively coupled to said box wherein said interior space is enclosed;
a valve coupled to said box, said valve extending through said lid wherein said canister is in an inverted position when said dispensing nozzle is engaged to said valve;
a canister having a dispensing nozzle, said dispensing nozzle being selectively engageable to said valve wherein contents of said canister are dispensed into said interior space of said box when said dispensing nozzle is engaged to said valve, said dispensing nozzle being positioned at a bottom of an interior space of said canister when said canister is in said inverted position;
an anesthetizing agent positioned in said canister, said anesthetizing agent being one anesthetizing agent selected from a group of anesthetizing agents consisting of nitrous oxide and isoflurane, said anesthetizing agent being a liquid in said canister, said anesthetizing agent producing a concentration of between 10% and 50% nitrous oxide within said interior space of said box when nitrous oxide is dispersed into said interior space of said box, said anesthetizing agent producing a concentration of between 1% and 8% isoflurane within said interior space of said box when said anesthetizing agent is dispensed into said interior space of said box;
a euthanizing agent positioned in said canister, said euthanizing agent being a gas in said canister wherein said anesthetizing agent is dispensed through said dispensing nozzle prior to said euthanizing agent being dispensed into said interior space of said box, said euthanizing agent being dispensed from said canister subsequent to said anesthetizing agent when said dispensing nozzle is engaged to said valve, said euthanizing agent being a hemoglobin binding agent, said euthanizing agent being carbon monoxide producing a concentration between 1,000 parts per million and 20,000 parts per million within said interior space of said box when said euthanizing agent is dispersed into said interior space of said box, said anesthetizing agent and said euthanizing agent each being dispensed into said interior space of said box in sequence by a single connection of said dispensing nozzle to said valve;
a restrictor coupled to said valve, said restrictor having an opening therethrough sized such that said anesthetizing agent is dispensed through said restrictor as a pre-selected rate wherein said anesthetizing agent anesthetizes an animal in said interior space of said box prior to said euthanizing agent being dispersed into said interior space of said box;
a vent aperture extending through said box;
a vent closure coupled to said box, said vent closure selectively sealing said vent aperture wherein said interior space of said box is sealed when said lid is in a closed position and said vent closure is in a closed position;
an exhaust mechanism coupled to said box, said exhaust mechanism being environmentally coupled to said vent closure wherein gaseous contents of said interior space of said box is vented through said vent aperture when said exhaust mechanism is actuated;

a propellant being positioned in said canister, said propellant facilitating dispensation of said anesthetizing agent and said anesthetic agent from said canister when said dispensing nozzle is coupled to said valve;

a cavity positioned on a dispensing end of said canister, said dispensing nozzle being positioned in said cavity;

an exterior wall of said dispensing nozzle being threaded; and said valve having complimentary threading wherein said canister is threadedly coupled to said box for dispensing said contents of said canister into said interior space of said box.

* * * * *